US008026651B2

(12) United States Patent
Wakabayashi et al.

(10) Patent No.: US 8,026,651 B2
(45) Date of Patent: Sep. 27, 2011

(54) ULTRASOUND TRANSDUCER AND ELECTRONIC DEVICE

(75) Inventors: Katsuhiro Wakabayashi, Hachioji (JP); Hideo Adachi, Iruma (JP); Kazuya Matsumoto, Nagano (JP); Mamoru Hasegawa, Nagano (JP); Kazuhisa Karaki, Nagano (JP); Yoshitaka Kamiya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 373 days.

(21) Appl. No.: 12/424,118

(22) Filed: Apr. 15, 2009

(65) Prior Publication Data

US 2009/0262605 A1 Oct. 22, 2009

(30) Foreign Application Priority Data

Apr. 16, 2008 (JP) ................................ 2008-107038

(51) Int. Cl.
*H01L 41/04* (2006.01)
*A61B 8/00* (2006.01)

(52) U.S. Cl. ......... 310/344; 367/181; 600/437; 600/459

(58) Field of Classification Search .................. 310/334; 367/181; 600/437, 459
See application file for complete search history.

(56) References Cited

U.S. PATENT DOCUMENTS

| | | | | |
|---|---|---|---|---|
| 7,275,298 | B2 * | 10/2007 | Schindel | 29/594 |
| 7,940,603 | B2 * | 5/2011 | Adachi et al. | 367/181 |
| 2007/0057603 | A1 * | 3/2007 | Azuma et al. | 310/334 |
| 2007/0161896 | A1 * | 7/2007 | Adachi et al. | 600/437 |
| 2009/0058228 | A1 * | 3/2009 | Wakabayashi et al. | 310/334 |
| 2009/0202083 | A1 * | 8/2009 | Kageyama | 381/59 |
| 2011/0108838 | A1 * | 5/2011 | Kageyama | 257/49 |

FOREIGN PATENT DOCUMENTS

| | | |
|---|---|---|
| EP | 1 781 067 A1 | 5/2007 |
| EP | 2030698 A1 * | 3/2009 |
| JP | 2005-510264 | 4/2005 |
| JP | 2006-319713 | 11/2006 |
| WO | 03/035281 A2 | 5/2003 |

OTHER PUBLICATIONS

Abstract of WO 03/011749 A2, dated Feb. 13, 2003.

* cited by examiner

*Primary Examiner* — Jaydi San Martin

(74) *Attorney, Agent, or Firm* — Scully, Scott, Murphy & Presser, P.C.

(57) ABSTRACT

An ultrasound transducer includes a substrate, an ultrasound transducer cell placed on one surface of the substrate and having a lower electrode, a first gap portion placed on the lower electrode and an upper electrode placed on the first gap portion, a first conductive layer placed on the other surface of the substrate and electrically connected to one of the lower electrode and the upper electrode, an electret film placed on the first conductive layer, an insulating layer placed on the electret film, and a second conductive layer placed on the insulating layer and electrically connected to the one of the lower electrode and the upper electrode not electrically connected to the first conductive layer.

10 Claims, 8 Drawing Sheets

ULTRASOUND TRANSDUCER AND ELECTRONIC DEVICE

This application claims benefit of Japanese Application No. 2008-107038 filed in Japan on Apr. 16, 2008, the contents of which are incorporated by this reference.

BACKGROUND OF THE INVENTION

1. Field of the Invention

The present invention relates to a capacitive ultrasound transducer configured by having an electret and an electronic device.

2. Description of the Related Art

Piezoelectric elements made of a ceramic piezoelectric material PZT (lead zirconate titanate) have been chiefly used as an ultrasound transducer. In recent years, a capacitive ultrasound transducer such as the one disclosed in Japanese Patent Application Laid-Open Publication No. 2005-510264 has attracted attention.

The capacitive ultrasound transducer is configured by having a pair of electrodes formed of an upper electrode and a lower electrode facing each other through a gap portion formed therebetween, and transmits or receives ultrasound through vibration of a membranous portion including the upper electrode (also referred to as "membrane" or "diaphragm").

The capacitive ultrasound transducer converts an ultrasound signal into an electrical signal on the basis of changes in electrostatic capacity between the upper and lower electrodes when receiving ultrasound and, therefore, requires application of a DC bias voltage between the upper and lower electrodes particularly at the time of reception.

From the viewpoint of reducing the power consumption and size of an ultrasound transducer, it is preferable to reduce or set to zero the voltage value of the DC bias voltage. As a technique to reduce the DC bias voltage, a technique of producing a potential difference between the upper and lower electrodes of the capacitive ultrasound transducer by providing between the upper and lower electrodes an electret film holding electric charge is known.

SUMMARY OF THE INVENTION

An ultrasound transducer according to the present invention includes a substrate, an ultrasound transducer cell placed on one surface of the substrate and having a lower electrode, a first gap portion placed on the lower electrode and an upper electrode placed on the first gap portion, a first conductive layer placed on the other surface of the substrate and electrically connected to one of the lower electrode and the upper electrode, an electret film placed on the first conductive layer, an insulating layer placed on the electret film, and a second conductive layer placed on the insulating layer and electrically connected to the one of the lower electrode and the upper electrode not electrically connected to the first conductive layer.

The above and other objects, features and advantages of the invention will become more clearly understood from the following description referring to the accompanying drawings.

DETAILED DESCRIPTION OF THE PREFERRED EMBODIMENTS

A preferred embodiment of an ultrasound transducer will be described below with reference to the accompanying drawings. In the figures referred to in the following description, the scales on which components are drawn are changed so that the components are shown in such sizes as to be recognizable in the figures. The present invention is not limited to the numbers and shapes of the components, the ratios of the sizes of the components and the relative positional relationships between the components shown in the figures.

Figure 1:
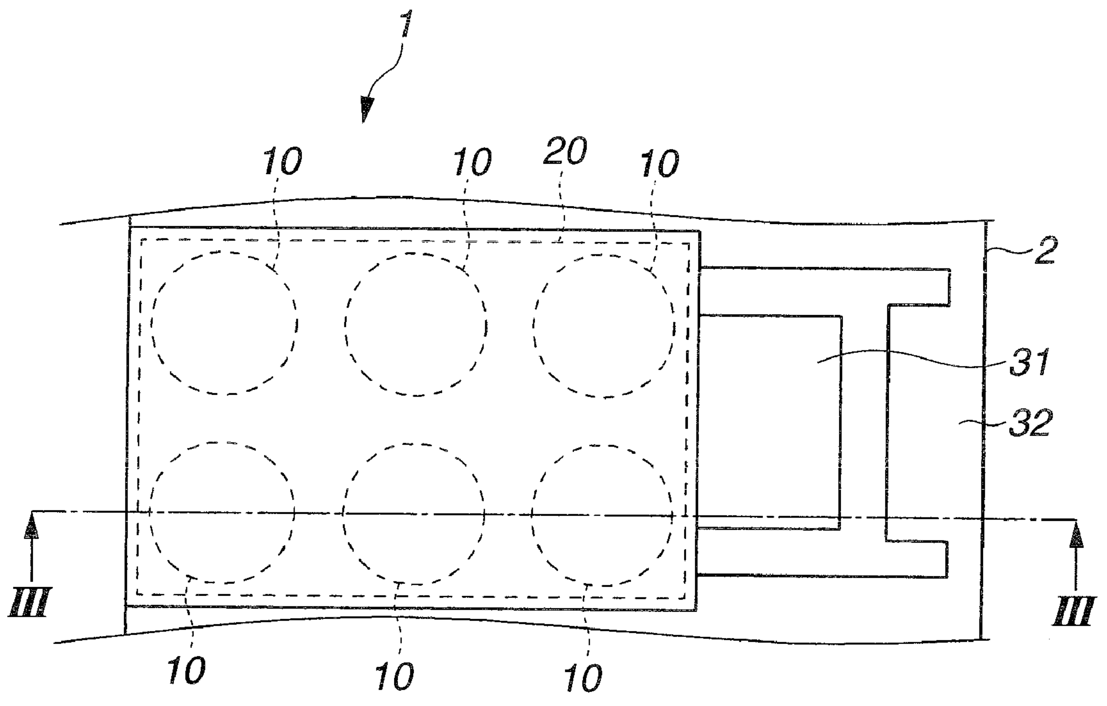
FIG. 1 is a plan view of an ultrasound transducer seen in a direction of transmission of ultrasound.
Figure 2:
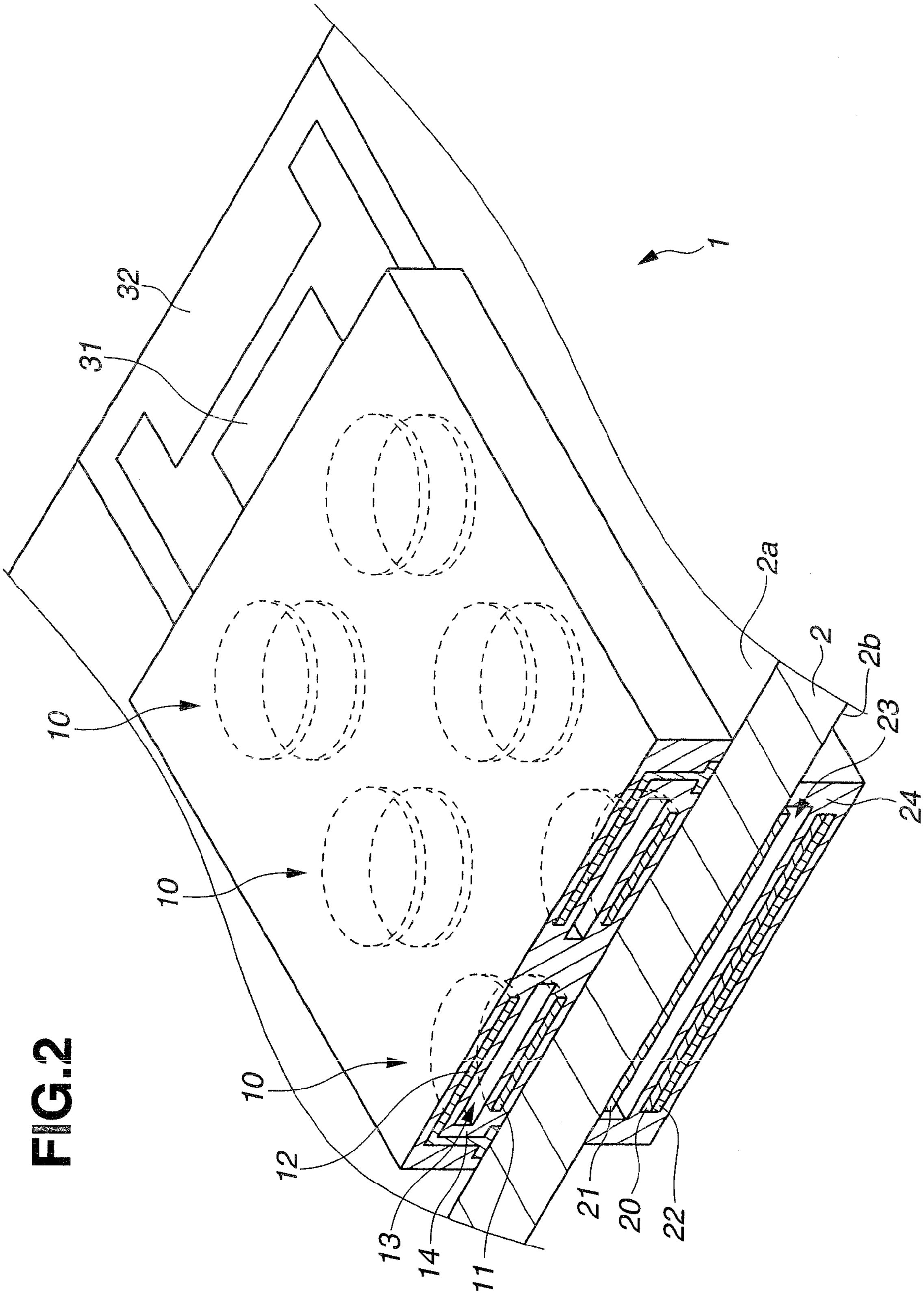
FIG. 2 is a schematic perspective view of a configuration of the ultrasound transducer.
Figure 3:
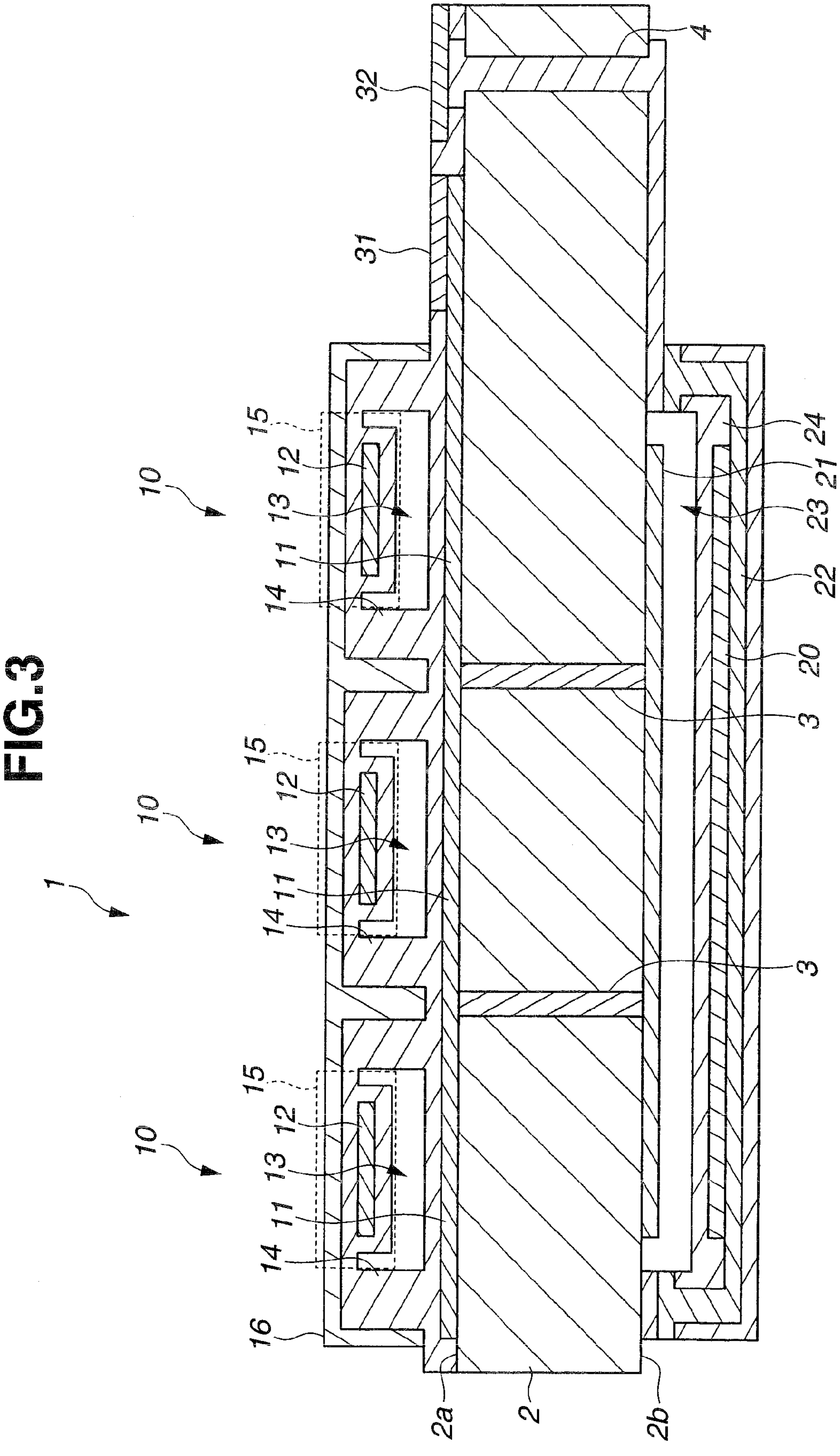
FIG. 3 is a sectional view taken along line III-III in FIG. 1.
Figure 4:
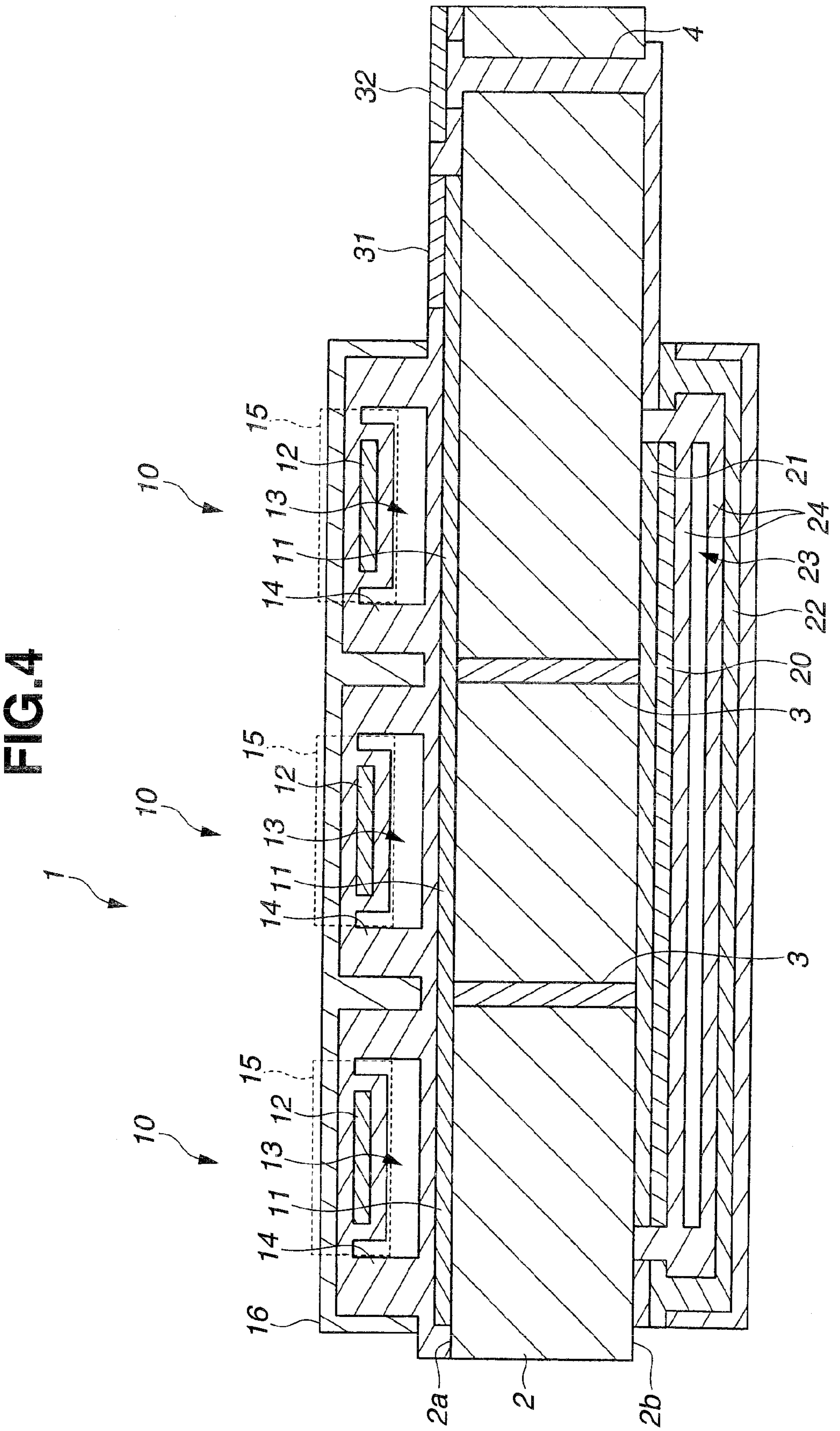
FIG. 4 is a sectional view of a modified example of the ultrasound transducer.

FIG. 1 is a plan view of an ultrasound transducer seen in the direction of transmission of ultrasound. FIG. 2 is a schematic perspective view of a configuration of the ultrasound transducer. FIG. 3 is a sectional view taken along line III-III in FIG. 1. FIG. 4 is a sectional view of a modified example of the ultrasound transducer.

An ultrasound transducer 1 has an ultrasound transducer cell 10 provided on one surface 2*a* of a substrate 2, and an electret film 20 provided on the other surface 2*b* of the substrate 2.

The positional relationship in the top-bottom direction between two components provided on the one surface 2*a* or the other surface 2*b* of the substrate 2 is defined in such a manner that the one of the components remoter from the surface than the other in the direction of a normal to the surface is referred to as the upper one. For example, in the sectional view shown in FIG. 3, an upper electrode 12 is described as being provided above a lower electrode 11 on the one surface 2*a* of the substrate 2, and a second conductive layer 22 is described as being provided above a first conductive layer 21 on the other surface 2*b* of the substrate 2.

The material forming the substrate 2 is not limited to a particular one. The substrate 2 may be formed of a material having an electrically conductive property or a material having an electrically insulating property. In the present embodiment, the substrate 2 is formed of a publicly insulating material, such as a silicon oxide, a silicon nitride, quartz, sapphire, crystallized quartz, alumina, zirconia, glass or a resin.

The ultrasound transducer cell 10 is configured by having the lower electrode 11 in the form of a flat plate provided on the one surface 2*a* of the substrate 2, and the upper electrode 12 in the form of a flat plate provided above the lower electrode 11 so as to face the lower electrode 11 through a first gap portion 13 formed therebetween.

The upper electrode 12 is supported generally parallel to the lower electrode 11 by an insulating layer 14 provided on the lower electrode 11 and formed of a material having an electrically insulating property. When the ultrasound transducer cell 10 transmits or receives ultrasound, a membranous portion 15 including the upper electrode 12 and the insulating layer 14 positioned above the first gap portion 13 vibrates.

It is preferred from the viewpoint of acoustic characteristics that the shape of the membranous portion 15 as seen in a direction perpendicular to the major surfaces of the substrate 2 is circular, as illustrated. However, the shape of the membranous portion 15 may alternatively be oval, elliptic or polygonal. In a case where a plurality of ultrasound transducer cells 10 are provided in one ultrasound transducer 1, the ultrasound transducer cells 10 may have a plurality of types of membranous portions 15 having different shapes.

It is preferred that the insulating layer 14 is provided so as to cover at least one of the surface of the lower electrode 11 on the first gap portion 13 side and the surface of the upper electrode 12 on the first gap portion 13 side and have the function to prevent the lower electrode 11 and the upper electrode 12 from contacting and shorting to each other.

In the present embodiment, the lower electrode 11 is electrically connected to a signal electrode pad 31 formed on the surface 2*a* of the substrate 2, as shown in FIG. 3. The upper electrode 12 is electrically connected by wiring not shown to a ground electrode pad 32 formed on the surface 2*a* of the substrate 2.

The signal electrode pad 31 and the ground electrode pad 32 are electrodes provided in a state of being exposed at such positions as not to overlap the ultrasound transducer cell 10 as seen in a direction perpendicular to the surface 2*a* of the substrate 2. A drive circuit which drives the ultrasound transducer 1 is electrically connected to the ultrasound transducer cell 10 via the signal electrode pad 31 and the ground electrode pad 32.

A protective film 16 made of a resin may be provided on the ultrasound transducer cell 10, for example, as shown in FIG. 3, for the purpose of preventing oxidization, preventing damage, improving moisture resistance, or the like.

On the other surface 2*b* of the substrate 2 opposite from the surface on which the above-described ultrasound transducer cell 10 is provided, the electret film 20 for producing a potential difference between the lower electrode 11 and the upper electrode 12 of the ultrasound transducer cell 10 is provided.

The configuration on the other surface 2*b* of the substrate 2 will be described in detail. The first conductive layer 21 in the form of a flat plate formed of an electrically conductive material is first provided on the other surface of the substrate 2. The first conductive layer 21 is electrically connected to the lower electrode 11 via a through electrode 3 in a via hole formed through the substrate 2.

The electret film 20 is provided above the first conductive layer 21. An insulating layer having an electrically insulating property is interposed between the first conductive layer 21 and the electret film 20. The electret film 20 is a publicly electret film having the function to permanently hold positive or negative charge. The method of configuring and forming the electret film 20 is not particularly specified.

For example, if the electret film 20 is formed of an inorganic film, the electret film 20 is formed by injecting charge into an inorganic film formed of a silicon compound, a hafnium compound or the like by means of an ion beam or corona discharge. The electret film 20 may have a multilayer structure formed of a plurality of kinds of material. For example, it is preferable that the electret film 20 is formed of $SiO_2$ and is covered with an insulating film formed of SiN because dissipation of held charge is limited even under a high-temperature condition.

For example, if the electret film 20 is formed of an organic film, the electret film 20 is formed by injecting charge into a resin film formed of fluororesin, polyimide, polypropylene, polymethylpentene or the like by means of corona discharge.

In the present embodiment, the insulating layer interposed between the first conductive layer 21 and the electret film 20 is configured of a second gap portion 23 and an insulating film 24 formed of a material having an electrical insulating property.

The insulating layer interposed between the first conductive layer 21 and the electret film 20 is not limited to this form. For example, the insulating layer may be in such a form that the electret film 20 and the first conductive layer 21 are electrically insulated from each other only by the second gap portion 23 or only by the insulating film 24.

Covering the surface of the electret film 20 with the insulating film 24 as in the present embodiment is more preferable because dissipation of charge held by the electret film 20 can be limited thereby.

The second conductive layer 22 in the form of a flat plate formed of an electrically conductive material and opposed generally parallel to the first conductive layer 21 is provided on the electret film 20, i.e., on the side of the electret film 20 opposite from the first conductive layer 21 side. The electret film 20 and the second conductive layer 22 may be provided in contact with each other, or an electrically conductive or electrically insulating film capable of preventing oxidization of the surface of the second conductive layer 22 may be interposed between the electret film 20 and the second conductive layer 22.

The second conductive layer 22 is electrically connected to the ground electrode pad 32 via a through electrode 4 in a via hole formed through the substrate 2. That is, the second conductive layer 22 is electrically connected to the upper electrode 12.

The configuration for electrically connecting the first conductive layer 21 and the second conductive layer 22 to the lower electrode 11 and the upper electrode 12 in the present embodiment is not exclusively adopted. For example, a configuration may alternatively be adopted in which the first conductive layer 21 and the second conductive layer 22 are electrically connected to the lower electrode 11 and the upper electrode 12 via pieces of wiring provided so as to extend along an outer peripheral portion of the substrate 2 in a roundabout fashion.

The above-described electret film 20 and the second conductive layer 22 are supported by the insulating film 24. In other words, the insulating film supports the electret film 20 and the second conductive layer 22 so that the second gap portion 23 is formed between the electret film 20 and the first conductive layer 21, and so that the first conductive layer 21 and the second conductive layer 22 are generally parallel to each other.

If, as shown in FIG. 3, the second gap portion 23 is formed as a closed space, i.e., in an airtight manner, and if the surface of the first conductive layer 21 is exposed in the second gap portion 23, it is preferable to evacuate the second gap portion 23 or to fill the second gap portion 23 with a dry inert gas for the purpose of preventing oxidization of the first conductive layer 21. If the second gap portion is not formed in an airtight manner, it is preferable to cover the surface of the first conductive layer 21 with a protective film for preventing oxidization.

The arrangement including the electret film 20 may alternatively be such that, as shown in FIG. 4, the electret film 20 is provided on the first conductive layer 21 in contact with the same; the insulating layer formed of the insulating film 24 containing the second gap portion 23 is provided on the electret film 20; and the second conductive layer 22 is provided on the insulating layer.

The effects of the ultrasound transducer 1 having the above-described configuration will be described below.

In the ultrasound transducer 1 having the above-described configuration, the electret film 20 for causing a potential difference between the lower electrode 11 and the upper electrode 12 of the ultrasound transducer cell 10 is provided on the surface (2*b*) of the substrate 2 opposite from the surface (2*a*) on which the ultrasound transducer cell 10 is provided.

In the ultrasound transducer 1 according to the present embodiment, therefore, the thickness of the electret film 20 and the distance between the lower electrode 11 and the upper electrode 12 can be set independently of each other.

That is, according to the present embodiment, in contrast with the conventional capacitive ultrasound transducer having an electret film provided between upper and lower electrodes, the distance between the lower electrode 11 and the upper electrode 12 is reduced to increase the electrostatic capacity between these electrodes, thereby improving the sound pressure of transmitted ultrasound and the sensitivity to received ultrasound. Also, the thickness of the electret film 20 can be increased to such a value as to be capable of permanently holding charge with stability.

By having the electret film 20, therefore, the ultrasound transducer 1 according to the present embodiment has an output and sensitivity higher than those of the conventional ultrasound transducer while reducing the DC bias voltage applied between the lower electrode 11 and the upper electrode 12 or eliminating the need for application of the DC bias voltage.

The ultrasound transducer according to the present embodiment is capable of increasing the thickness of the electret film 20 in comparison with the conventional ultrasound transducer and is, therefore, capable of stabilizing the charge holding performance of the electret film 20 and maintaining the performance for a long time period.

In the present embodiment, the electret film 20 is provided at such a position as to be superposed on the ultrasound transducer cell 10 as seen in a direction perpendicular to the major surfaces of the substrate 2 and, therefore, the ultrasound transducer 1 according to the present embodiment can be realized in the same size as the conventional ultrasound transducer in which an electret film is provided between upper and lower electrodes.

In general, some ultrasound transducer is used in a state of having the surface for transmitting or receiving ultrasound maintained in contact with a liquid for the purpose of enabling ultrasound to propagate without being attenuated. On the other hand, in some case, the electret film 20 loses charge by contact with moisture. In the present embodiment, the electret film 20 is provided on the side opposite from the surface for transmitting or receiving ultrasound, thereby enabling prevention of permeation of moisture into the electret film 20 and improving the durability of the ultrasound transducer 1.

With the conventional ultrasound transducer having an electret film provided between upper and lower electrodes, there is a problem that charge held by the electret film dissipates under the influence of components of an atmosphere, humidity and temperature in a manufacturing process performed after injecting charge in the electret film. Conventionally, therefore, there are only a limited number of processing methods executable after injection of charge into a material forming the electret film or after injection of charge into the electret film.

In contrast, in manufacturing the above-described ultrasound transducer 1, the ultrasound transducer cell 10 to be provided on the surface 2*a* of the substrate 2 and the electret film 20 to be provided on the other surface 2*b* of the substrate 2 can be combined after being respectively manufactured separately from each other.

Therefore, the electret film 20 can be provided in the ultrasound transducer 1 without being placed in an environment which may cause dissipation of charge held by the electret film 20 after injection of charge into the electret film 20. That is, the ultrasound transducer 1 having the above-described configuration has an improved degree of design freedom with which a selection from construction materials, a selection from processing methods and the like are made and can therefore be implemented with improved performance at a lower price in comparison with the conventional ultrasound transducer. Because of the improvement in the degree of design freedom with which construction materials are selected, the ultrasound transducer 1 can be constituted of a material of a reduced environmental load, for example, a lead-free material.

The above-described ultrasound transducer 1 can be manufactured by using various manufacturing techniques such as a semiconductor manufacturing technique and a micromachining technique. Therefore, the method of forming the ultrasound transducer 1 is not particularly specified. However, a micro-electro-mechanical system (MEMS) process for example may be used. An ultrasound transducer made by a MEMS process is ordinarily called a capacitive micromachined ultrasonic transducer (c-MUT).

Examples of electronic devices to which the ultrasound transducer of the present invention can be applied will be described with reference to FIGS. 5 to 9.

Figure 5:
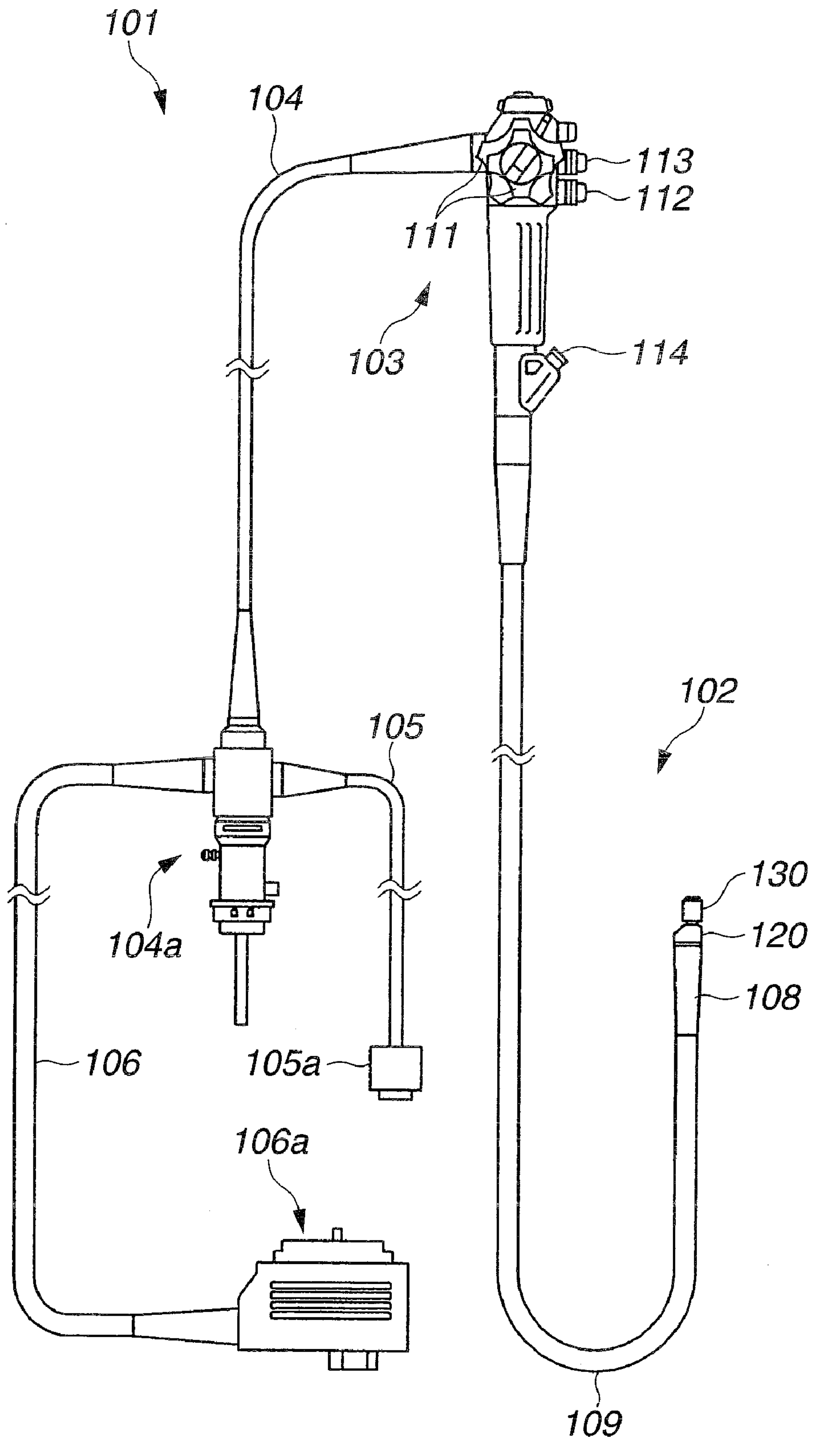
FIG. 5 is a diagram schematically showing a configuration of an ultrasound endoscope.
Figure 6:
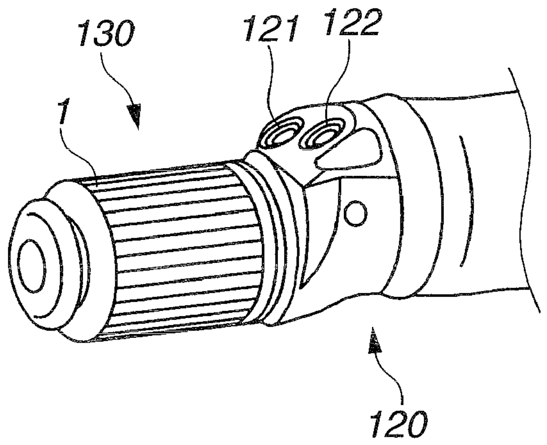
FIG. 6 is a perspective view of a distal end portion of the ultrasound endoscope.
Figure 7:
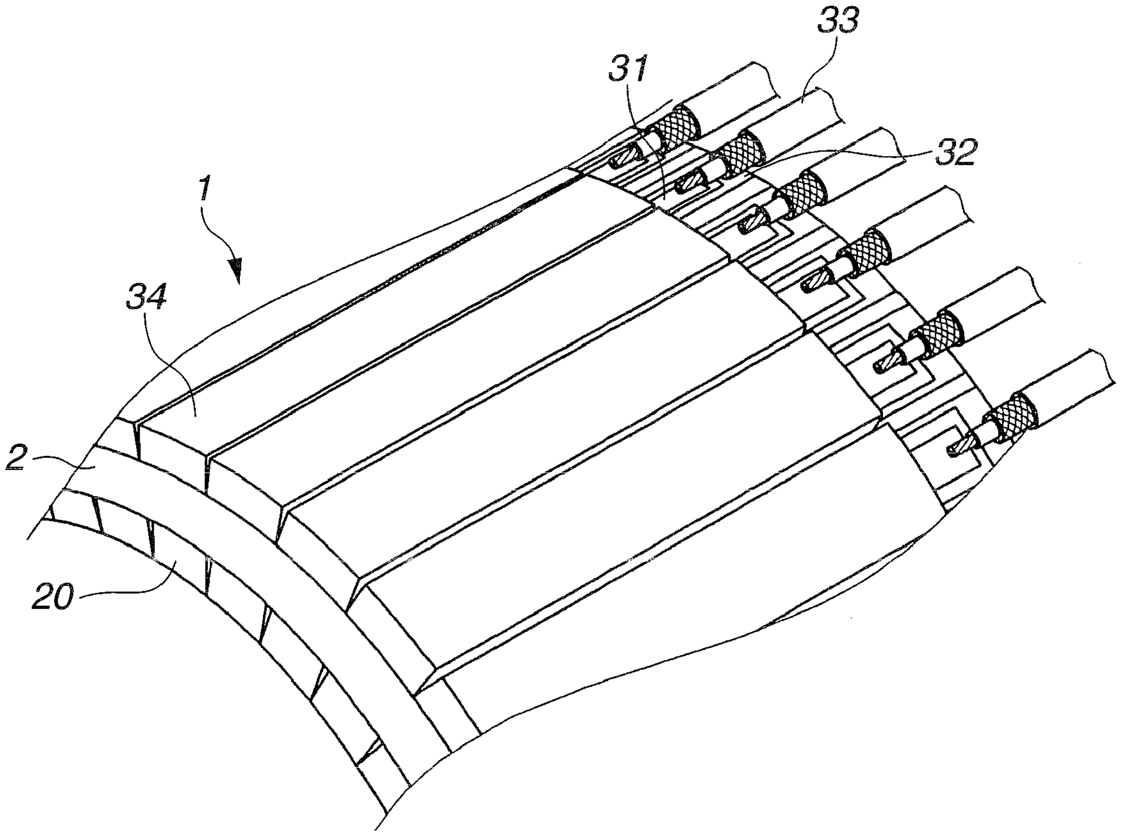
FIG. 7 is a perspective view of an ultrasound transmitting/receiving portion.

A mode in which the ultrasound transducer 1 of the present invention is applied to an ultrasound endoscope as an example of an ultrasound diagnostic apparatus will be described with reference to FIGS. 5 to 7. FIG. 5 is a diagram schematically showing a configuration of an ultrasound endoscope. FIG. 6 is a perspective view of a configuration of a distal end portion of the ultrasound endoscope. FIG. 7 is a perspective view of an ultrasound transmitting/receiving portion.

As shown in FIG. 5, an ultrasound endoscope 101 in the present embodiment is configured mainly of an elongated insertion portion 102 to be inserted into the body of a subject, an operation portion 103 positioned at a proximal end of the insertion portion 102, and a universal cord 104 extending from a side portion of the operation portion 103.

An endoscope connector 104*a* to be connected to a light source device (not shown) is provided on a proximal end portion of the universal cord 104. From the endoscope connector 104*a*, an electric cable 105 detachably connected to a camera control unit (not shown) through an electric connector 105*a* extends. An ultrasound cable 106 detachably connected to an ultrasound observation apparatus (not shown) through an ultrasound connector 106*a* also extends from the endoscope connector 104*a*.

The insertion portion 102 is configured by providing, in order from the distal end side, one adjacent to another, a distal end rigid portion 120 formed of a rigid member, a bending portion 108 capable of bending operation positioned at a rear end of the distal end rigid portion 120, and a flexible tube portion 109 positioned at a rear end of the bending portion 108, extending to a distal end portion of the operation portion 103, small in diameter, elongated and having flexibility. An ultrasound transmitting/receiving portion 130 for transmitting or receiving ultrasound, described below, is provided on the distal end side of the distal end rigid portion 120.

The operation portion 103 is provided with an angle knob 111 for controlling the bending portion 108 in bending in a desired direction, air supply and water supply button 112 for performing air supply and water supply operations, a suction button 113 for performing a suction operation, and a treatment instrument insertion opening 114, which is an inlet for a treatment instrument to be introduced into a body cavity.

As shown in FIG. 6, the distal end rigid portion 120 is provided with an illumination lens (not shown) constituting an illumination optical section for irradiating illumination light to a portion to be observed, an objective lens 121 constituting an observation optical section for capturing an optical image of a portion to be observed, an opening 122 for suction and for forceps, through which a excised part is sucked in or a treatment instrument is projected, and air supply and water supply opening (not shown) for air supply and water supply.

In the ultrasound transmitting/receiving portion 130 provided on the distal end of the distal end rigid portion 120, as shown in FIG. 7, a plurality of ultrasound transducers 1 are configured being arrayed in cylindrical form, with ultrasound transducer cells 10 facing radially outwardly.

A substrate 2 is constituted of a material having flexibility, e.g., polyimide and is rounded into a cylindrical shape. On an outer peripheral surface of the substrate 2 rounded into a cylindrical shape, ultrasound transducer elements 34 each constituted of a plurality of ultrasound transducer cells 10 and provided as a smallest drive unit are arrayed along a circumferential direction, and electrets 20 corresponding to the plurality of ultrasound transducer elements 34 are provided on an inner peripheral surface of the substrate 2.

Signal electrode pads 31 and ground electrode pads 32 corresponding to the plurality of ultrasound transducer elements 34 are formed on the outer peripheral surface of the substrate 2. Ends of coaxial cables 33 passed through an ultrasound cable 106 are electrically connected to the signal electrode pads 31 and the ground electrode pads 32. Other ends of the coaxial cables are passed through the ultrasound cable 106 to be electrically connected to the ultrasound connector 106*a*.

The ultrasound transducer 1 of the present invention is applicable to publicly ultrasound diagnosis apparatuses as well as to the above-described ultrasound endoscope. For example, the ultrasound transducer 1 may be applied to an ultrasound probe type of ultrasound endoscope, a capsule type of ultrasound endoscope or to an ultrasound diagnosis apparatus arranged to transmit ultrasound from the outside of a subject into the subject and receive ultrasound from the subject.

Figure 8:
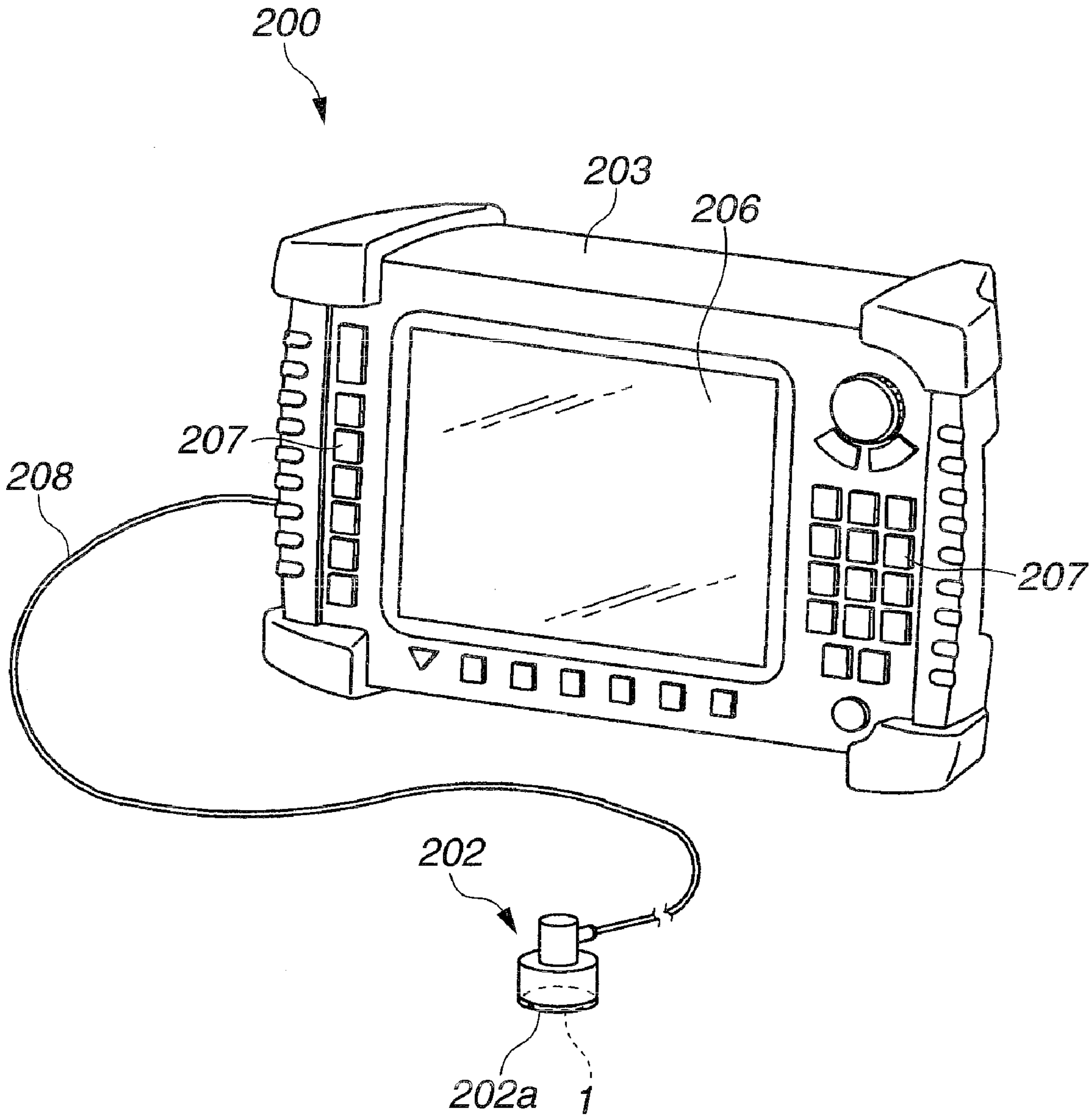
FIG. 8 is a diagram schematically showing a configuration of an ultrasound flaw detection apparatus.

A mode in which the ultrasound transducer 1 of the present invention is applied to an ultrasound flaw detection apparatus as an example of a nondestructive inspection apparatus will be described with reference to FIG. 8. FIG. 8 is a diagram schematically showing a configuration of an ultrasound flaw detection apparatus.

An ultrasound flaw detection apparatus 200 has a probe 202 for transmitting and receiving ultrasound, and an apparatus main unit 203 for controlling the probe 202.

A display device 206 which displays an image for flaw detection is provided at a center of a front face of the apparatus main unit 203, and switches 207 having various roles are provided in the vicinity of the display device 206.

The probe 202 is connected to the apparatus main unit 203 by a composite coaxial cable 208. One ultrasound transducer 1 or a plurality of ultrasound transducers 1 are provided in a contact surface portion 202*a* of the probe 202 to be brought into contact with a subject.

The ultrasound flaw detection apparatus 200 issues ultrasound while maintaining the contact surface portion 202*a* of the probe 202 in contact with a subject and can detect a flaw in the subject through a change in reflection of the ultrasound without breaking the subject.

The ultrasound transducer 1 of the present invention is applicable to publicly nondestructive inspection apparatuses as well as to the above-described ultrasound flaw detection apparatus. For example, the ultrasound transducer 1 may be applied to a thickness measuring apparatus for measuring the thickness of a subject by transmitting and receiving ultrasound.

Figure 9:
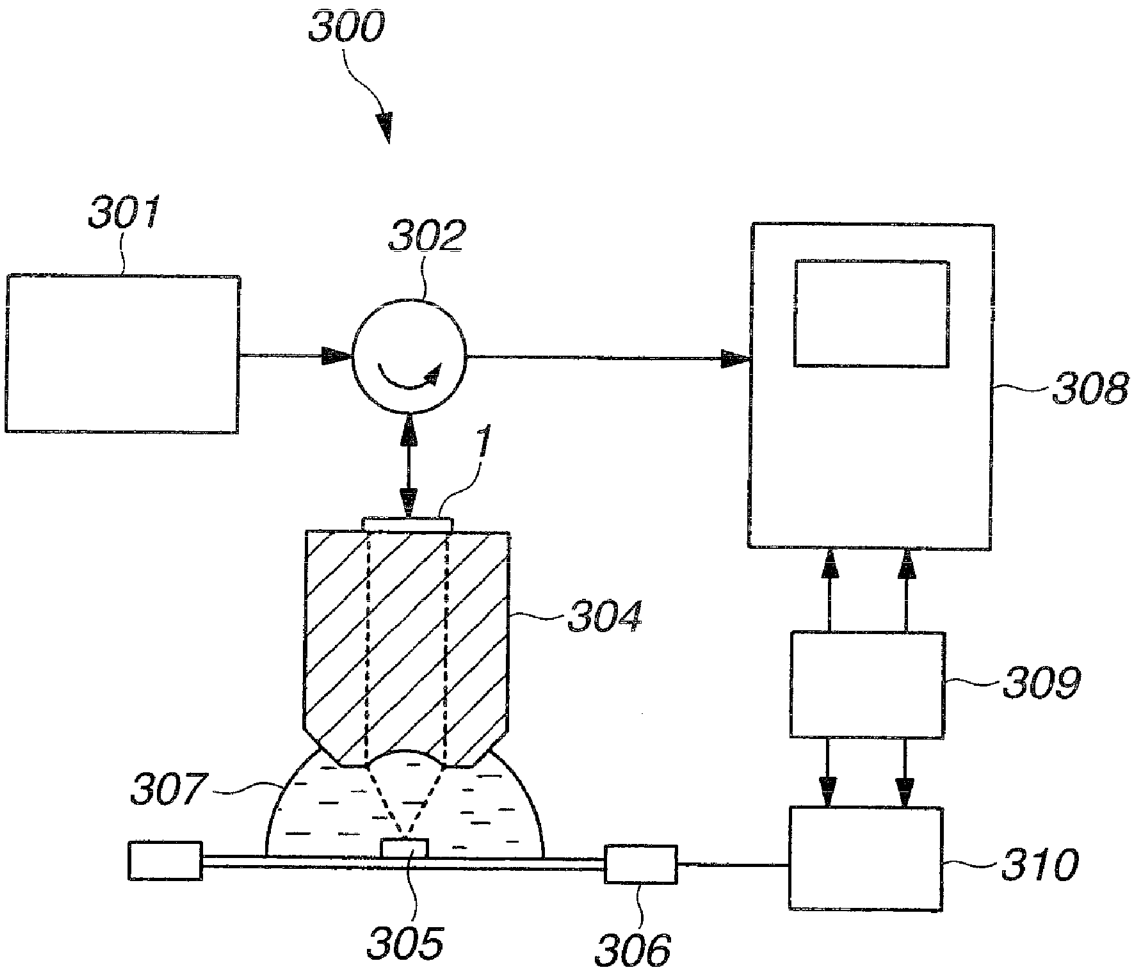
FIG. 9 is a diagram schematically showing a configuration of an ultrasound microscope.

An example of an application of the ultrasound transducer 1 of the present invention to an ultrasound microscope will be described with reference to FIG. 9. FIG. 9 is a diagram showing a configuration of an ultrasound microscope in the present embodiment.

An ultrasound microscope 300 applies a radiofrequency signal generated in a radiofrequency oscillator 301 to an ultrasound transducer 1 according to the present invention through a circulator 302 to convert the radiofrequency signal into ultrasound. This ultrasound is converged with an acoustic lens 304. At the point of this convergence, a specimen 305 is placed. The specimen 305 is held by a sample holder 306 and a space between the specimen 305 and the lens surface of the acoustic lens 304 is filled with a coupler 307 such as water. Reflected waves from the specimen 305 are received by the transducer 1 through the acoustic lens 304 to be converted into an electrical reflection signal. The electric signal outputted from the ultrasound transducer 1 in correspondence with the received ultrasound is inputted to a display device 308 through the circulator 302. The sample holder 306 is driven in a horizontal plane in directions along two axes: X- and Y-axes by a scanning device 310 controlled by a scanning circuit 309.

The ultrasound microscope 300 configured as described above can quantify an elastic characteristic of the specimen 305 by applying ultrasound to the specimen 305 and evaluating an acoustic characteristic of the specimen 305 and can evaluate the structure of a thin film.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasound transducer comprising:

a substrate;

an ultrasound transducer cell placed on one surface of the substrate and having a lower electrode, a first gap portion placed on the lower electrode and an upper electrode placed on the first gap portion;

a first conductive layer placed on the other surface of the substrate and electrically connected to one of the lower electrode and the upper electrode;

an electret film placed on the first conductive layer;

an insulating layer placed on the electret film; and a second conductive layer placed on the insulating layer and electrically connected to the one of the lower electrode and the upper electrode not electrically connected to the first conductive layer.

2. The ultrasound transducer according to claim 1, wherein the insulating layer includes a pair of insulating films and a second gap portion interposed between the pair of insulating films.

3. The ultrasound transducer according to claim 2, wherein the substrate has flexibility.

4. The ultrasound transducer according to claim 1, wherein the substrate has flexibility.

5. An electronic device comprising the ultrasound transducer according to claim 1.

6. An ultrasound transducer comprising:

a substrate;

an ultrasound transducer cell placed on one surface of the substrate and having a lower electrode, a first gap portion placed on the lower electrode and an upper electrode placed on the first gap portion;

a first conductive layer placed on the other surface of the substrate and electrically connected to one of the lower electrode and the upper electrode;

an insulating layer placed on the first conductive layer;

an electret film placed on the insulating layer; and a second conductive layer placed on the electret film and electrically connected to the one of the lower electrode and the upper electrode not electrically connected to the first conductive layer.

7. The ultrasound transducer according to claim 6, wherein the insulating layer includes a pair of insulating films and a second gap portion interposed between the pair of insulating films.

8. The ultrasound transducer according to claim 7, wherein the substrate has flexibility.

9. The ultrasound transducer according to claim 6, wherein the substrate has flexibility.

10. An electronic device comprising the ultrasound transducer according to claim 6.

* * * * *

UNITED STATES PATENT AND TRADEMARK OFFICE

CERTIFICATE OF CORRECTION

PATENT NO. : 8,026,651 B2
APPLICATION NO. : 12/424118
DATED : September 27, 2011
INVENTOR(S) : Katsuhiro Wakabayashi et al.

It is certified that error appears in the above-identified patent and that said Letters Patent is hereby corrected as shown below:

On the title page item (73), should read:

(73) Assignee: Olympus Medical Systems Corp., Tokyo (JP)
Olympus Corporation, Tokyo (JP)

Signed and Sealed this
Thirty-first Day of January, 2012

David J. Kappos
*Director of the United States Patent and Trademark Office*